US012745923B2

(12) United States Patent
Suleman et al.

(10) Patent No.: US 12,745,923 B2
(45) Date of Patent: Sep. 29, 2026

(54) SYSTEM AND METHOD FOR DETERMINING USER-SPECIFIC ESTIMATION WEIGHTS FOR SYNTHESIZING SENSOR READINGS

(71) Applicant: Orpyx Medical Technologies Inc., Calgary (CA)

(72) Inventors: Omar Suleman, Vancouver (CA); Samuel Carl William Blades, Victoria (CA)

(73) Assignee: ORPYX MEDICAL TECHNOLOGIES INC., Calgary (CA)

(*) Notice: Subject to any disclaimer, the term of this patent is extended or adjusted under 35 U.S.C. 154(b) by 538 days.

(21) Appl. No.: 18/183,642

(22) Filed: Mar. 14, 2023

(65) Prior Publication Data

US 2023/0293044 A1 Sep. 21, 2023

Related U.S. Application Data

(60) Provisional application No. 63/320,805, filed on Mar. 17, 2022.

(51) Int. Cl.
*A61B 5/103* (2006.01)

(52) U.S. Cl.
CPC ...... *A61B 5/1036* (2013.01); *A61B 2562/043* (2013.01)

(58) Field of Classification Search
CPC ............ A61B 5/1036; A61B 2562/043; A61B 5/1123; A61B 5/112; A61B 5/4561;
(Continued)

(56) References Cited

U.S. PATENT DOCUMENTS

| | | | | |
|---|---|---|---|---|
| 9,591,993 | B2 * | 3/2017 | Morris Bamberg | A61B 5/0002 |
| 2010/0211355 | A1 * | 8/2010 | Horst | G01G 23/3735 73/172 |

(Continued)

FOREIGN PATENT DOCUMENTS

| | | | |
|---|---|---|---|
| KR | 102260470 | B1 | 11/2020 |
| WO | 2021092676 | A1 | 5/2021 |

OTHER PUBLICATIONS

S. Yin, C. Chen, H. Zhu, X. Wang and W. Chen, "Neural Networks for Pathological Gait Classification Using Wearable Motion Sensors," 2019 IEEE Biomedical Circuits and Systems Conference (BioCAS), Nara, Japan, 2019, pp. 1-4, doi: 10.1109/BIOCAS.2019.8919096. (Year: 2019).*

(Continued)

*Primary Examiner* — Tse W Chen
(74) *Attorney, Agent, or Firm* — ABM INTELLECTUAL PROPERTY INC.; Adrienne Bieber McNeil

(57) ABSTRACT

A system, method and computer program product for determining user-specific weights usable to synthesize sensor data at void locations in a sensor array. Initial estimation weights are determined for the void locations. Sensor readings are obtained from a plurality of sensors while a user performs predefined actions. The sensors are arranged in a first pattern that maps the sensors to respective locations on the wearable device. Synthesized sensor readings are determined based on the sensor readings and the initial estimation weights. User-specific weights are determined by modifying the initial estimation weights using an aggregate force value determined from the obtained sensor readings. The user-specific weights can be used to determine synthesized sensor readings at void locations for the user. The sensor array can be mounted to a carrier device such as a wearable device worn by the user or fitness equipment used by the user.

18 Claims, 5 Drawing Sheets

(58) Field of Classification Search
CPC ................ A61B 5/6895; A61B 5/7267; A61B 2562/046; A61B 5/6807; A61B 5/1038
See application file for complete search history.

(56) References Cited

U.S. PATENT DOCUMENTS

| | | | | |
|---|---|---|---|---|
| 2011/0054358 | A1 | 3/2011 | Kim et al. | |
| 2014/0343889 | A1 | 11/2014 | Shalom et al. | |
| 2019/0304331 | A1 * | 10/2019 | Karapetyan ............ | G09B 19/00 |
| 2019/0314185 | A1 * | 10/2019 | Yuge ...................... | A63B 23/08 |

OTHER PUBLICATIONS

Todd C. Pataky, Spatial resolution in plantar pressure measurement revisited, Journal of Biomechanics, 2012, pp. 2116-2124, 45(12).
M. Holtzman et al., Force Estimation with a Non-Uniform Pressure Sensor Array, 2008 IEEE Instrumentation and Measurement Technology Conference, 2008, pp. 1974-1979.
Sarah Ostadabbas et al., Continuous Plantar Pressure Modeling Using Sparse Sensors, 2012 IEEE 12th International Conference on BioInformatics & BioEngineering (BIBE), 2012, pp. 309-314.
Sarah Ostadabbas, A Knowledge-Based Modeling for Plantar Pressure Image Reconstruction, IEEE Transactions on Biomedical Engineering, 2014, pp. 2538-2549, 61(10).
Wangjoo Lee et al., Characterization of Elastic Polymer-Based Smart Insole and a Simple Foot Plantar Pressure Visualization Method Using 16 Electrodes, Sensors, 2019, 19(1), pp. 44-53.
Alfredo Ciniglio et al., The Design and Simulation of a 16-Sensors Plantar Pressure Insole Layout for Different Applications: From Sports to Clinics, a Pilot Study, 2021, 21(4), pp. 1450-1471.

* cited by examiner

SYSTEM AND METHOD FOR DETERMINING USER-SPECIFIC ESTIMATION WEIGHTS FOR SYNTHESIZING SENSOR READINGS

CROSS-REFERENCE TO RELATED APPLICATIONS

This application claims the benefit of priority of U.S. Provisional Application No. 63/320,805 filed Mar. 17, 2022, which is incorporated herein by reference.

FIELD

This document relates to systems and methods for processing data from sensors monitoring human movement or human activity. In particular, this document relates to synthesizing sensor data at locations between, and outside of, sensors monitoring human movement or human activity.

BACKGROUND

United States Patent Application Publication No. 2011/054358A1 (Kim et al.) discloses a gait/posture analysis method which analyzes a gait/posture of a walker wearing a shoe having one or more pressure sensors attached thereon. The gait/posture analysis method includes: measuring a base foot pressure, which is generated when the walker wears the shoe, at arbitrary time intervals; calculating a representative base foot pressure by using the plurality of base foot pressures measured at the arbitrary time intervals; correcting a foot pressure measured by the pressure sensors by using the representative base foot pressure; calculating a foot-pressure related value, which is to be used for analyzing the gait/posture of the walker, by using the corrected foot pressure; and analyzing the gait/posture of the walker by using the foot-pressure related value.

United States Patent Application Publication No. 2014/343889A1 (Ben Shalom et al.) discloses a system supporting subject risk analysis and risk event management for detecting possible risk indications and the risk of a subject developing pressure injuries. The system includes monitoring risk events using a pressure sensing apparatus and by recording pressure values at a plurality of pixels of a sensing mat to determine subject's pressure distribution and associated pressure image at any given time. The mapping of pressure sensing elements coordinates of the pressure sensing apparatus to a subject-based coordinate system using applicable transformation functions enables risk analysis and display of subject's pressure distribution maps representing gathered data at different times. Pressure images of the subject's pressure distributions helps in identifying postures adopted by a subject, determining risk of a subject developing pressure injuries and registering possible bed-exit and bed-fall risk events.

SUMMARY

The following summary is intended to introduce the reader to various aspects of the detailed description, but not to define or delimit any invention.

A system, method and computer program product for determining user-specific weights usable to synthesizing sensor data is provided. More particularly, in some examples, a plurality of sensors can be provided in a predetermined arrangement in a sensing unit for equipment or a wearable device. The sensors can be configured to acquire readings relating to human movement or human activity. The predetermined arrangement can include void locations between, and outside, the plurality of sensors. An initial set of estimation weights can be determined for the void locations, e.g. using interpolation/extrapolation methods or generic user data. Training data can be determined for a particular user based on measured sensor readings obtained from the plurality of sensors while the user performs a predefined action. The training data can be used to modify the initial set of estimation weights in order to define user-specific weights usable to synthesize sensor data for the particular user. The user-specific weights can improve the accuracy of synthesized sensor data for individual users.

According to some aspects, the present disclosure provides a method of determining user-specific weights usable to synthesize sensor data at void locations of a sensor array. The method includes determining a plurality of initial estimation weights for the void locations; obtaining a plurality of measured sensor readings from a corresponding plurality of sensors in the sensor array, wherein the plurality of sensors is arranged in a first predetermined pattern, wherein the first predetermined pattern maps each of the plurality of sensors to respective locations on a carrier device, wherein the plurality of measured sensor readings includes at least one measured sensor set, and wherein each measured sensor set is collected while a user performs a corresponding predefined action; determining a training sensor set for each measured sensor set by: estimating a plurality of synthesized sensor readings for a corresponding plurality of synthesized sensors based on the plurality of measured sensor readings from that measured sensor set and the plurality of initial estimation weights, wherein the plurality of synthesized sensors is arranged in a second predetermined pattern, and wherein the second predetermined pattern maps each of the plurality of synthesized sensors to respective void locations of the sensor array; and determining the training sensor set to include the measured sensor readings from that measured sensor set and the corresponding plurality of synthesized sensor readings; determining the user-specific weights by: determining at least one aggregate force value based on the at least one training sensor set; and modifying the initial estimation weights based on the at least one aggregate force value; and outputting the user-specific weights.

Determining the user-specific weights can include: determining at least one error value based on the at least one aggregate force value; and modifying the initial estimation weights to reduce the at least one error value.

The at least one measured sensor set can include a plurality of measured sensor sets, each measured sensor set can correspond to a different predefined action, and determining the user-specific weights can include: determining a plurality of aggregate force values based on the training sensor sets corresponding to the plurality of measured sensor sets; and determining the at least one error value by comparing pairs of aggregate force values from the plurality of aggregate force values.

The at least one error value can include at least one relative error value, and each relative error value can be determined based on a difference in the total force magnitude of the aggregate force values in a corresponding pair of aggregate force values.

The at least one error value can include at least one relative error value, and each relative error value can be determined based on a difference in the total force magnitude between a given aggregate force value and a mean aggregate force value of the plurality of aggregate force values.

The at least one error value can include at least one absolute error value, and each absolute error value can be determined based on a difference in the total force magnitude between a particular aggregate force value and a known bodyweight of the user.

The method can include determining a cost function based on the at least one error value, and adjusting the initial estimation weights using an optimization algorithm to optimize the cost function.

The at least one error value can include a plurality of error values, and the cost function can be determined as a combination of the plurality of error values.

Each predefined action can correspond to a user standing in a static standing position, and each measured sensor set can correspond to a particular static standing position.

The carrier device can be a wearable device or fitness equipment. The fitness equipment can be a bicycle seat. The fitness equipment can be an exercise mat, a fitness bench, an exercise bar, or a treadmill.

The carrier device can be a wearable device worn by the user. The wearable device can be worn by a foot. The wearable device can be an insole.

The sensors can be force sensors.

The plurality of sensors can be positioned underfoot.

The carrier device can be a wearable device worn by the user, and outputting the user-specific weights can include storing the user-specific weights in a non-transitory storage module of the wearable device.

The plurality of measured sensor readings can be obtained while the wearable device is worn by the user.

According to some aspects, there is also provided a system for determining user-specific weights usable to synthesize sensor data at void locations of a sensor array. The system includes the sensor array, including a plurality of sensors arranged in a first predetermined pattern, with each sensor of the plurality of sensors arranged at a respective location on a carrier device; and one or more processors communicatively coupled to the plurality of sensors. The one or more processors is configured to: obtain a corresponding plurality of sensor readings from the plurality of sensors in the sensor array, wherein the plurality of measured sensor readings includes at least one measured sensor set, and each measured sensor set is collected while a user performs a corresponding predefined action; determine a training sensor set for each measured sensor set by: estimating a plurality of synthesized sensor readings for a corresponding plurality of synthesized sensors based on the plurality of measured sensor readings from that measured sensor set and the plurality of initial estimation weights, the plurality of synthesized sensors arranged in a second predetermined pattern, wherein the second predetermined pattern maps each of the plurality of synthesized sensors to respective void locations of the sensor array; and determining the training sensor set to include the measured sensor readings from that measured sensor set and the corresponding plurality of synthesized sensor readings; determine the user-specific weights by: determining at least one aggregate force value based on the at least one training sensor set; and modifying the initial estimation weights based on the at least one aggregate force value; and output the user-specific weights.

The one or more processors can be configured to determine the user-specific weights by: determining at least one error value based on the at least one aggregate force value, and modifying the initial estimation weights to reduce the at least one error value.

The at least one measured sensor set can include a plurality of measured sensor sets. Each measured sensor set can correspond to a different predefined action, and the one or more processors can be configured to determine the user-specific weights by: determining a plurality of aggregate force values based on the training sensor sets corresponding to the plurality of measured sensor sets; and determining the at least one error value by comparing pairs of aggregate force values from the plurality of aggregate force values.

The one or more processors can be configured to determine the at least one error value to include at least one relative error value. Each relative error value can be determined based on a difference in the total force magnitude of the aggregate force values in a corresponding pair of aggregate force values.

The one or more processors can be configured to determine the at least one error value to include at least one relative error value. Each relative error value can be determined based on a difference in the total force magnitude between a given aggregate force value and a mean aggregate force value of the plurality of aggregate force values.

The one or more processors can be configured to determine the at least one error value to include at least one absolute error value. Each absolute error value can be determined based on a difference in the total force magnitude between a particular aggregate force value and a known bodyweight of the user.

The one or more processors can be configured to determine a cost function based on the at least one error value, and adjust the initial estimation weights using an optimization algorithm to optimize the cost function.

The one or more processors can be configured to determine the at least one error value to include a plurality of error values, and determine the cost function as a combination of the plurality of error values.

Each predefined action can correspond to a user standing in a static standing position, and each measured sensor set can correspond to a particular static standing position.

The carrier device can be a wearable device or fitness equipment. The fitness equipment can be a bicycle seat. The fitness equipment can be an exercise mat, a fitness bench, an exercise bar, or a treadmill.

The carrier device can be a wearable device worn by the user. The wearable device can be worn by a foot. The wearable device can be an insole.

The sensors can be force sensors.

The plurality of sensors can be positioned underfoot.

The carrier device can be a wearable device and the one or more processors can be configured to output the user-specific weights by storing the user-specific weights in a non-transitory storage module of the wearable device.

The plurality of measured sensor readings can be obtained while the wearable device is worn by the user.

According to some aspects, there is provided a non-transitory computer readable medium storing computer-executable instructions, which, when executed by a computer processor, cause the computer processor to carry out a method for determining user-specific weights usable to synthesize sensor data at void locations of a sensor array. The method includes: determining a plurality of initial estimation weights for the void locations; obtaining a plurality of measured sensor readings from a corresponding plurality of sensors in the sensor array, wherein the plurality of sensors is arranged in a first predetermined pattern, wherein the first predetermined pattern maps each of the plurality of sensors to respective locations on a carrier device, wherein the plurality of measured sensor readings includes at least one measured sensor set, and wherein each measured sensor set is collected while a user performs a corresponding predefined action; determining a training sensor set for each measured sensor set by: estimating a plurality of synthesized sensor readings for a corresponding plurality of synthesized sensors based on the plurality of measured sensor readings from that measured sensor set and the plurality of initial estimation weights, wherein the plurality of synthesized sensors is arranged in a second predetermined pattern, and wherein the second predetermined pattern maps each of the plurality of synthesized sensors to respective void locations of the sensor array; and determining the training sensor set to include the measured sensor readings from that measured sensor set and the corresponding plurality of synthesized sensor readings; determining the user-specific weights by: determining at least one aggregate force value based on the at least one training sensor set; and modifying the initial estimation weights based on the at least one aggregate force value; and outputting the user-specific weights.

The non-transitory computer readable medium can be configured to store computer-executable instructions, which, when executed by a computer processor, cause the computer processor to carry out a method for determining user-specific weights, where the method is described herein.

A system, method and computer program product for synthesizing sensor data using user-specific estimation weights is provided. More particularly, in some examples, a plurality of sensors can be provided in a predetermined arrangement in a sensing unit for equipment or a wearable device. The sensors can be configured to acquire readings relating to human movement or human activity. Based on sensor readings received from the plurality of sensors and a set of user-specific estimation weights that are optimized for a particular user, sensor readings at locations between the sensors can be estimated. Sensor readings at locations outside the set of sensors can also be estimated using the user-specific estimation weights. This may provide the sensing system with high resolution and high-fidelity sensor readings while reducing the complexity and cost of the sensing unit. The user-specific estimation weights may account for differences in stances and gait between users that can affect sensor readings.

According to some aspects, there is provided a method for synthesizing sensor data for a user. The method includes: obtaining a plurality of sensor readings from a corresponding plurality of sensors, wherein the plurality of sensors are arranged in a first predetermined pattern, and wherein the first predetermined pattern maps each of the plurality of sensors to respective locations on a carrier device; based on the plurality of sensor readings and a plurality of user-specific weights calculated for the user, estimating a plurality of synthesized sensor readings for a corresponding plurality of synthesized sensors, wherein the plurality of synthesized sensors are arranged in a second predetermined pattern, and wherein the second predetermined pattern maps each of the plurality of synthesized sensors to respective locations on the carrier device; and outputting the plurality of sensor readings and the plurality of synthesized sensor readings.

The plurality of user-specific weights can be determined according to the methods as described herein.

The carrier device can be a wearable device or fitness equipment. The fitness equipment can be a bicycle seat. The fitness equipment can be an exercise mat, a fitness bench, an exercise bar, or a treadmill.

According to some aspects, there is provided a system for synthesizing sensor data for a user. The system includes: a plurality of sensors arranged in a first predetermined pattern, with each sensor of the plurality of sensors arranged at a respective location on a carrier device; and one or more processors communicatively coupled to the plurality of sensors, wherein the one or more processors is configured to: obtain a plurality of sensor readings from a corresponding plurality of sensors, wherein the plurality of sensors are arranged in a first predetermined pattern, and wherein the first predetermined pattern maps each of the plurality of sensors to respective locations on the carrier device; based on the plurality of sensor readings and a plurality of user-specific weights calculated for the user, estimate a plurality of synthesized sensor readings for a corresponding plurality of synthesized sensors, wherein the plurality of synthesized sensors are arranged in a second predetermined pattern, and wherein the second predetermined pattern maps each of the plurality of synthesized sensors to respective locations on the carrier device; and output the plurality of sensor readings and the plurality of synthesized sensor readings.

The plurality of user-specific weights can be determined according to the methods as described herein.

The carrier device can be a wearable device or fitness equipment. The fitness equipment can be a bicycle seat. The fitness equipment can be an exercise mat, a fitness bench, an exercise bar, or a treadmill.

According to some aspects, there is provided a non-transitory computer readable medium storing computer-executable instructions, which, when executed by a computer processor, cause the computer processor to carry out a method for synthesizing sensor data for a user. The method includes: obtaining a plurality of sensor readings from a corresponding plurality of sensors, wherein the plurality of sensors are arranged in a first predetermined pattern, and wherein the first predetermined pattern maps each of the plurality of sensors to respective locations on a carrier device; based on the plurality of sensor readings and a plurality of user-specific weights calculated for the user, estimating a plurality of synthesized sensor readings for a corresponding plurality of synthesized sensors, wherein the plurality of synthesized sensors are arranged in a second predetermined pattern, and wherein the second predetermined pattern maps each of the plurality of synthesized sensors to respective locations on the carrier device; and outputting the plurality of sensor readings and the plurality of synthesized sensor readings.

The plurality of user-specific weights can be determined according to the methods as described herein.

The carrier device can be a wearable device or fitness equipment. The fitness equipment can be a bicycle seat. The fitness equipment can be an exercise mat, a fitness bench, an exercise bar, or a treadmill.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Figure 1:
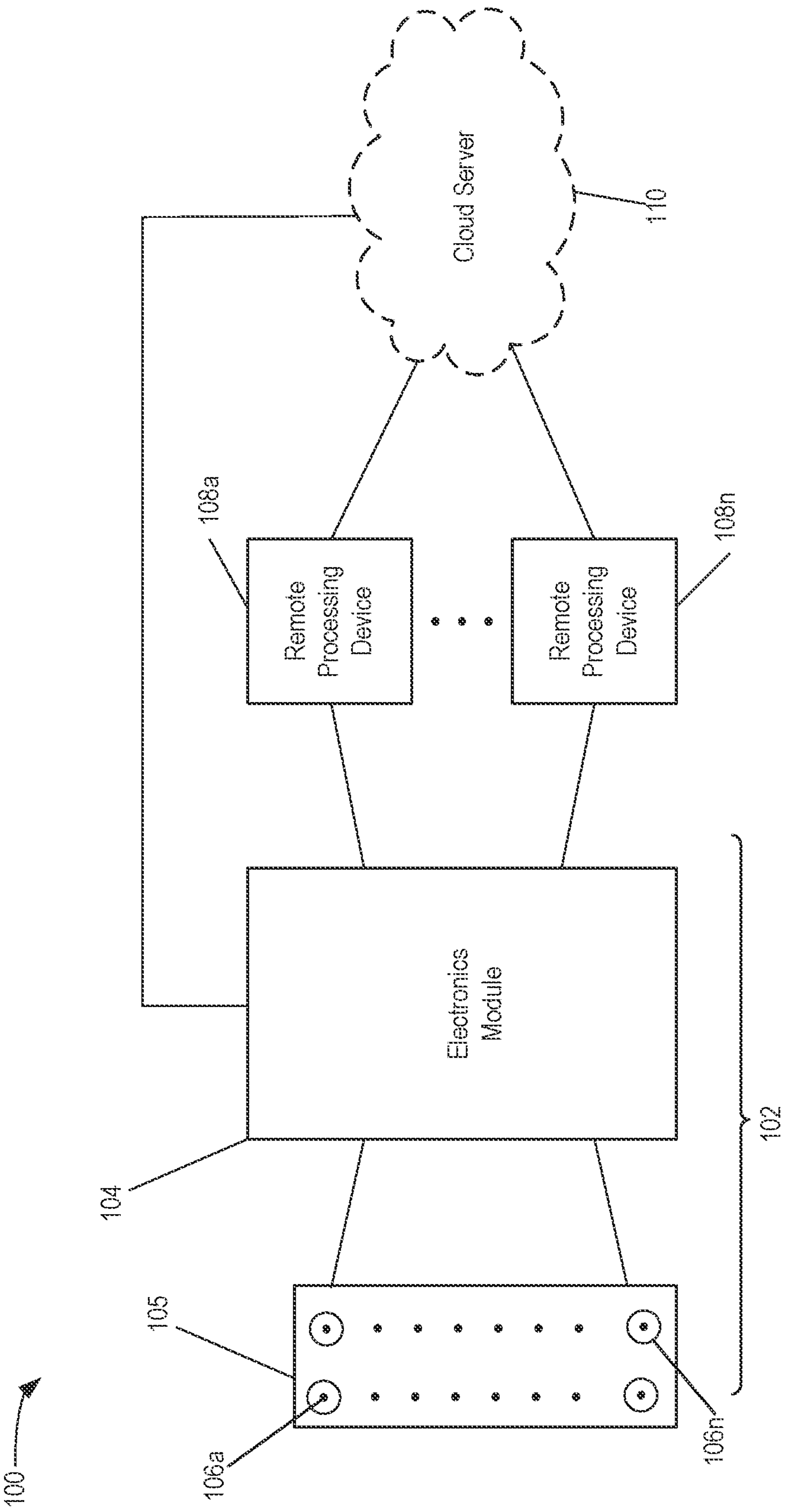
FIG. 1 is a block diagram illustrating an example of a system for synthesizing sensor data.

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

For simplicity and clarity of illustration, reference numerals may be repeated among the figures to indicate corresponding or analogous elements. In addition, numerous specific details are set forth in order to provide a thorough understanding of the subject matter described herein. However, it will be understood by those of ordinary skill in the art that the subject matter described herein may be practiced without these specific details. In other instances, well-known methods, procedures and components have not been described in detail so as not to obscure the subject matter described herein. The description is not to be considered as limiting the scope of the subject matter described herein.

The terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal, or a mechanical element depending on the particular context. Furthermore, the term "communicative coupling" may be used to indicate that an element or device can electrically, optically, or wirelessly send data to another element or device as well as receive data from another element or device.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are systems, methods and devices for determining user-specific weights usable to synthesize sensor data at void locations of a wearable device or fitness equipment. Also described herein are systems, methods and devices for synthesizing sensor data for a wearable device or fitness equipment. The systems, methods, and devices can use sensors attached to, or contained within, wearable devices or fitness equipment to measure and monitor data relating to movement or activity of an individual.

The sensors can be force sensors and can be provided in the insole of a shoe or within the footwear worn by the individual. As used herein, the term "force" is used broadly and can refer to raw force (i.e. with units of N), or pressure resulting from a raw force (i.e. with units of $N/m^2$). The force data acquired by the force sensors can be used to determine the level of force applied by an individual's foot when walking, running, or jumping for example. This force data can be used to derive additional force derivatives or force-based metrics, such as the force output or the center of pressure for the individual. The force data, and other data derived therefrom, can be used for tracking and monitoring various parameters that may be useful for medical, fitness, athletic, entertainment or other purposes.

The systems, methods, and devices described herein may be implemented as a combination of hardware or software. In some cases, the systems, methods, and devices described herein may be implemented, at least in part, by using one or more computer programs, executing on one or more programmable devices including at least one processing element, and a data storage element (including volatile and non-volatile memory and/or storage elements). These devices may also have at least one input device (e.g. a pushbutton keyboard, mouse, a touchscreen, and the like), and at least one output device (e.g. a display screen, a printer, a wireless radio, and the like) depending on the nature of the device.

Some elements that are used to implement at least part of the systems, methods, and devices described herein may be implemented via software that is written in a high-level procedural language such as object-oriented programming. Accordingly, the program code may be written in any suitable programming language such as Python or C for example. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods described herein may be capable of being distributed in a computer program product including a computer readable medium that bears computer usable instructions for one or more processors. The medium may be provided in various forms, including non-transitory forms such as, but not limited to, one or more diskettes, compact disks, tapes, chips, and magnetic and electronic storage. Alternatively, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The present disclosure relates to a system, method, and computer program product that can be used to determine user-specific estimation weights usable to synthesize sensor data based on sensor readings from a plurality of sensors. The plurality of sensors can be positioned in a predetermined arrangement. The sensors can be discrete sensors such that the predetermined arrangement includes void locations where no sensors are located. The void locations can include interstitial locations between the sensors as well as external locations outside the set of sensors. The subject matter described herein may be used to minimize error in synthesized sensor data at the interstitial locations between the discrete sensors when measuring human activity (such as human movement). The subject matter described herein may also be used to minimize error in synthesized sensor data at external void locations outside of a set of discrete sensors when measuring human activity.

Using a set of discrete sensors, as opposed to a dense continuous sensor array, can significantly reduce the cost of integrating sensing capabilities into a wearable device or piece of fitness equipment. When evaluating sensor data from a set of discrete sensors, interpolation techniques may be applied to estimate the sensed data at locations between the discrete sensors. However, traditional interpolation techniques between discrete sensors produce low accuracy estimates.

Similarly, extrapolation techniques may be applied to estimate the sensed data at locations external to the arrangement of discrete sensors. However, traditional extrapolation techniques at external void locations outside of a set of discrete sensors also tend to produce low accuracy estimates.

In addition, estimation weights generated based on generic user data may not account for the particulars of an individual's stance, gait, or stride. As will be described in further detail below, the subject matter described herein may increase the accuracy of sensor data estimates at locations between discrete sensors for individual users. The subject matter described herein may also increase the accuracy of sensor data estimates at locations outside an arrangement of discrete sensors for individual users.

In some examples, a plurality of sensors can be arranged in a first predetermined pattern that is mapped to respective locations on a wearable device or fitness equipment. A plurality of sensors readings can be received from the plurality of sensors.

Based on the plurality of sensor readings and a plurality of user-specific estimation weights, a plurality of synthesized sensor readings can be estimated for a corresponding plurality of synthesized sensors. The plurality of synthesized sensors can be arranged in a second predetermined pattern that maps each of the synthesized sensors to respective locations on the wearable device or fitness equipment.

The synthesized sensors may be mapped to locations where actual sensors are not present (i.e. void locations where there are no actual sensors on a wearable device or fitness equipment). The synthesized sensor readings can thus provide estimated sensor readings for locations between the plurality of sensors in the first predetermined pattern (i.e. interstitial locations where there are no actual sensors on a wearable device or fitness equipment). The synthesized sensor readings may also provide estimated sensor readings for locations external to the plurality of sensors in the first predetermined pattern (i.e. external void locations where there are no actual sensors on a wearable device or fitness equipment).

The plurality of sensor readings and the plurality of synthesized sensor readings can then be output. The output data can be used for various purposes, such as providing an individual with feedback on the sensor readings and/or for further analysis to determine derived sensor data.

The user-specific estimation weights can be defined individually for each user. The user-specific estimation weights can be determined using a plurality of initial estimation weights and training data obtained from the user. The training data can be used to modify the initial estimation weights in order to generate user-specific weights. The user-specific weights may then be applied to determine synthesized sensor readings for a sensor unit that is used by the same individual.

The initial estimation weights may be determined using training data from one or more individuals. These individuals can be different from the individual for whom the user-specific estimation weights are defined. The initial estimation weights may provide reasonable accuracy for synthesizing sensor readings for most users. However, by modifying the initial estimation weights based on sensor readings obtained for a specific user, the modified user-specific estimation weights can improve the accuracy of synthesizing sensor readings for that user even further. This may be particularly beneficial for users with unique or atypical strides or stances.

The user-specific estimation weights used to determine the synthesized sensor readings can be optimized during a preprocessing phase. Optimizing the estimation weights can help minimize the error between the estimated sensor readings (at location between discrete sensors and/or locations external to the set of discrete sensors) and actual sensor readings that would be acquired at the same locations (e.g. using a dense sensor array) when measuring human movement and human activity.

The preprocessing phase can reduce the computational expense required to determine the synthesized sensor readings when measuring human movement and human activity. In particular, optimizing the plurality of estimation weights during the preprocessing phase allows the user-specific estimation weights to be generated and stored prior to active data collection when the synthesized sensor readings are being determined. Accordingly, when sensor readings are acquired, the predetermined estimation weights can be used to easily and rapidly calculate real-time synthesized force data.

The preprocessing phase can include an initial training data collection process for a user. The user can be instructed to perform one or more predefined actions. Sensor readings can be obtained for each predefined action. Training data sets can be determined for the sensor readings associated with each predefined action. These training data sets can be used to determine the user-specific weights for that user. The training data sets can be used to modify initial estimation weights in order to determine optimized user-specific weights for that user.

The use of discrete sensors (also referred to as a sparse sensor array), as opposed to a more densely populated sensor array (referred to herein as a dense sensor array or continuous sensor array), can also reduce the volume of data that must be stored, managed and analyzed.

Referring now to FIG. 1, shown therein is a block diagram illustrating an example system 100 that can be used to determine user-specific weights usable to synthesize sensor data for a user. System 100 can also be used to synthesize sensor data for the user using the user-specific weights.

System 100 includes an input unit 102 (also referred to herein as an input device), one or more processing devices 108 (also referred to herein as a receiving device or an output device) and optionally a remote cloud server 110. As will be described in further detail below, the input unit 102 may for example be combined with, or integrated into, a carrier unit such as a wearable device or a piece of fitness equipment.

Input unit 102 generally includes a sensing unit 105. The sensing unit 105 can include a plurality of sensors **106*a*-106*n*. The plurality of sensors 106*a*-106*n* can be arranged in a first predetermined pattern that maps each sensor 106** to a corresponding location of the carrier unit.

The carrier unit can be configured to hold the sensors 106 in contact with (or close proximity to) an individual's body to allow the sensors 106 to measure an aspect of the activity being performed by the individual. The plurality of sensors **106*a*-106*n* may be configured to measure a particular sensed variable at a location of an individual's body when the carrier unit is engaged with the individual's body (e.g. when the individual is wearing a wearable device containing the sensors 106 or when the individual is using fitness equipment containing the sensors 106**).

In some examples, the carrier unit may include one or more wearable devices. The wearable devices can be manufactured of various materials such as fabric, cloth, polymer, or foam materials suitable for being worn close to, or in contact with, a user's skin. AD or a portion of the wearable device may be made of breathable materials to increase comfort while a user is performing an activity.

In some examples, the wearable device may be formed into a garment or form of apparel such as a band, headwear, a shirt, shorts, a sock, a shoe, a sleeve, and a glove (e.g. a tactile glove). Some wearable devices such as socks or sleeves may be in direct contact with a user's skin. Some wearable devices, such as shoes, may not be in direct contact with a user's skin but still positioned within sufficient proximity to a user's body to allow the sensors to acquire the desired readings.

In some cases, the wearable device may be a compression-fit garment. The compression-fit garment may be manufactured from a material that is compressive. A compression-fit garment may minimize the impact from "motion artifacts" by reducing the relative movement of the wearable device with respect to a target location on the individual's body. In some cases, the wearable device may also include anti-slip components on the skin-facing surface. For example, a silicone grip may be provided on the skin-facing surface of the wearable device to further reduce the potential for motion artifacts.

In some examples, the wearable device may be worn on a foot. For example, the wearable device may be a shoe, a sock, an insole or a portion of a shoe, a sock, or an insole. The wearable device may include a deformable material, such as foam. This may be particularly useful where the wearable device is worn underfoot, as in a shoe or insole.

The plurality of sensors **106*a*-106*n* can be positioned to acquire sensor reading from specified locations on an individual's body (via the arrangement of the sensors on the carrier unit). The sensors 106 can be integrated into the material of the carrier unit (e.g. integrated into a wearable device or fitness equipment). Alternatively, the sensors 106** can be affixed or attached to the carrier unit, e.g. printed, glued, laminated or ironed onto a surface, or between layers, of a wearable device or fitness equipment.

In some examples, the carrier unit may include fitness equipment. The fitness equipment may include various types of fitness equipment on which a user can exert force while performing an activity. For example, the carrier unit may be fitness equipment such as an exercise mat, a fitness bench, a bar (e.g. a squat rack or a pull-up bar), a treadmill, or a bicycle seat for a bicycle or stationary bicycle.

For clarity, the below description relates to a carrier unit in the form of an insole. The insole carrier unit may be provided in various forms, such as an insert for footwear or integrated into a shoe. However, other carrier units may be implemented using the systems and methods described herein, such as the wearable devices and fitness equipment described above.

The below description relates to an insole in which the plurality of sensors 106 are force sensors. However, alternative types of sensors, for which discrete sensor configurations and dense array sensor configurations exist, may be used. Such sensors may include, for example, optical sensors, temperatures sensors, or electromagnetic sensors.

In addition, various types of force sensors may be used, such as force sensing resistors (also referred to as "sensels" or sensing elements), pressure sensors, piezoelectric tactile sensors, elasto-resistive sensors, capacitive sensors or more generally any type of force sensor that can be integrated into a wearable device or fitness equipment.

Figure 2A:
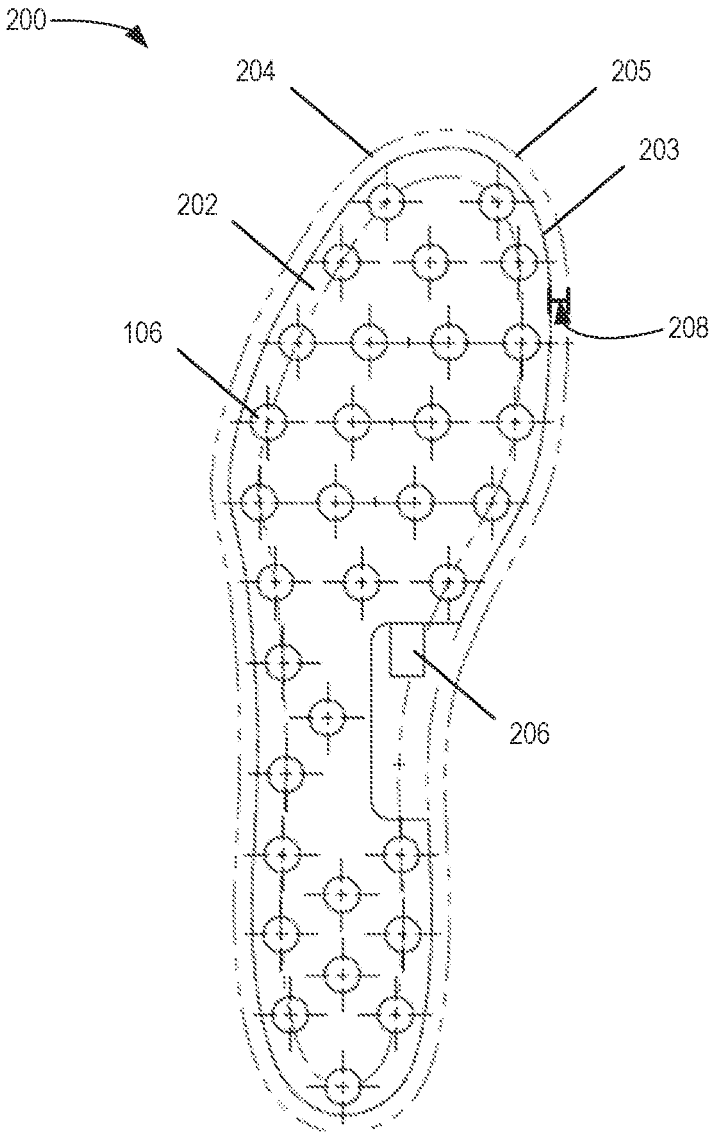
FIG. 2A is a diagram illustrating an example of a wearable device incorporating a sensing unit that can be used in the system of FIG. 1.
Figure 2B:
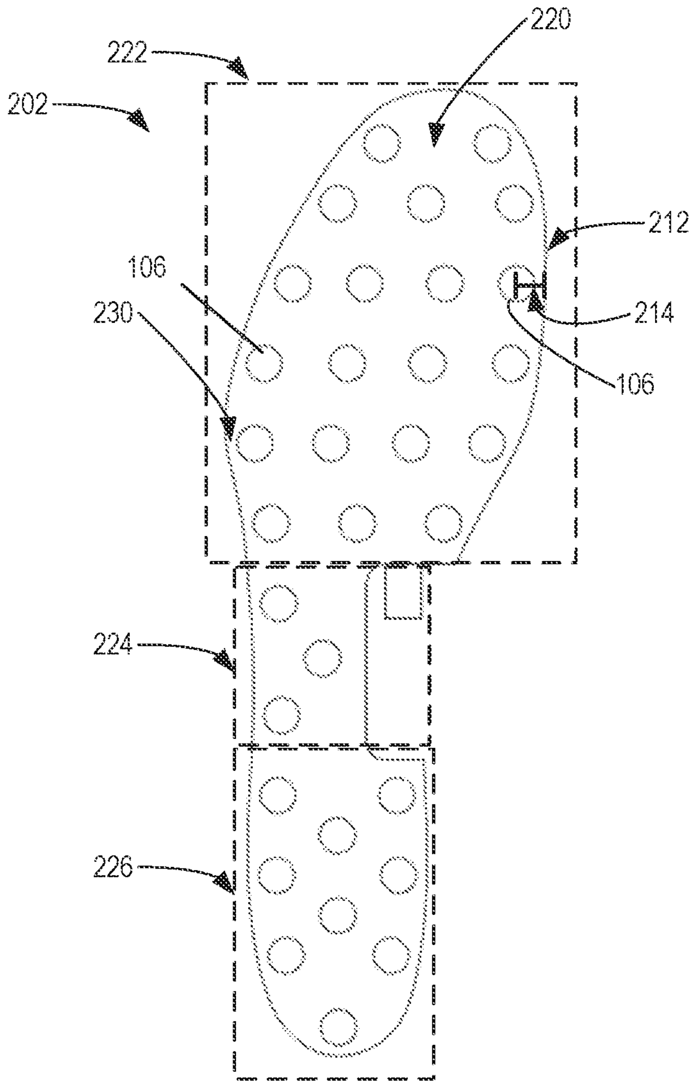
FIG. 2B is a diagram illustrating an example of a sensing unit that can be used with the wearable device of FIG. 2A.

The plurality of sensors 106 can be provided as a set of discrete sensors (see e.g. FIG. 2B). A discrete sensor is an individual sensor that acquires a sensor reading at a single location. A set of discrete sensors generally refers to multiple discrete sensors that are arranged in a spaced apart relationship in a sensing unit. The spaced apart relationship can define void locations where no sensors are located. The spaced apart relationship includes void locations in the form of gaps between the individual discrete sensors 106 (referred to herein as interstitial locations 220). No actual sensors are located in these interstitial locations 220. Similarly, the void locations can include locations (see locations 230 shown in FIG. 2B) external to the set of discrete sensors where synthesized sensor readings may be desired.

The sensors **106*a*-106*n* may be arranged in a sparse sensor array that includes void locations where no sensors 106** are located. A sensor array (as used herein) refers to a series of sensors arranged in a predefined layout. In a continuous or dense sensor array, in contrast to a set of discrete sensors that may provide a sparse sensor array, the sensors within the dense sensor array are arranged in a continuous, or substantially continuous manner, across the predefined layout. That is, a dense sensor array is considered to be capable of acquiring actual sensor readings at all locations of the sensor array. Thus, the dense sensor array does not typically need to estimate sensor values at interstitial locations or locations external to the array. The dense sensor array provides a comprehensive understanding of sensed values throughout the locations engaged by the corresponding layout.

Discrete sensors can provide an inexpensive alternative to dense sensor arrays for many applications. However, because no sensors are positioned in the interstitial locations 220 between the discrete sensors, no actual sensors readings can be acquired for the interstitial locations 220. Similarly, because no sensors are positioned in the void locations 230 external to the set of discrete sensors, no actual sensors readings can be acquired for the external void locations 230. In order to provide sensor data with similar resolution to a dense sensor array, sensor readings must be estimated (rather than measured) at the interstitial locations 220 and at the void locations 230 external to the set of discrete sensors.

Interpolation has been used to estimate the sensor values at the interstitial locations 220. Extrapolation has also been used to estimate the sensor values at the void locations 230 external to the set of discrete sensors. However, traditional interpolation and extrapolation often produces low accuracy estimates as compared to actual measurements taken at the corresponding locations with a dense sensor array.

Methods for synthesizing sensor data are also described in Applicant's co-pending patent application Ser. No. 17/988,468 filed on Nov. 16, 2022 entitled "SYSTEM AND METHOD FOR SYNTHESIZING SENSOR READINGS", the entirety of which is incorporated herein by reference. The present disclosure may involve modifying estimation weights determined using these methods to provide user-specific weights based on training data acquired from an individual user performing a predefined action.

System 100 can be configured to implement a method of determining user-specific weights for synthesizing sensor data that can increase the accuracy of estimated sensor readings between discrete sensors (i.e. at interstitial locations 220) and external to the set of discrete sensors (i.e. at external void locations) for a user. The user-specific weights may account for idiosyncrasies of the user's stance or gait. The method of determining user-specific weights may be implemented using a controller of the input device 102, a remote processing device 108, or cloud server 110.

System 100 can also be configured to implement a method of synthesizing sensor data using the user-specific weights. The method of synthesizing sensor data using the user-specific weights may be implemented using a controller of the input device 102, a remote processing device 108, or cloud server 110.

As shown in FIG. 1, input unit 102 includes an electronics module 104 coupled to the plurality of sensors 106. In some cases, the electronics module 104 can include a power supply, a processor, a memory, a signal acquisition unit operatively coupled to the processor and to the plurality of sensors 106, and a wireless communication module operatively coupled to the processor.

Generally, the sensing unit refers to the plurality of sensors 106 and the signal acquisition unit. The signal acquisition unit may provide initial analog processing of signals acquired using the sensors 106, such as amplification. The signal acquisition unit may also include an analog-to-digital converter to convert the acquired signals from the continuous time domain to a discrete time domain. The analog-to-digital converter may then provide the digitized data to the processor for further analysis or for communication to a remote processing device 108 or remote cloud server 110 for further analysis.

Optionally, the electronics module 104 may include a processor configured to perform the signal processing and analysis. In such cases, the processor on the electronics module may be configured to process the received sensor readings in order to determine synthesized sensor readings. In some cases, the processor may be coupled to the communication module (and thereby the sensing unit) using a wired connection such as Universal Serial Bus (USB) or other port.

The electronics module 104 can be communicatively coupled to one or more remote processing devices 108*a*-108*n*, e.g. using a wireless communication module (e.g., Bluetooth, Bluetooth Low-Energy, WiFi, ANT+ IEEE 802.11, etc.). The remote processing devices 108 can be any type of processing device such as a personal computer, a tablet, and a mobile device such as a smartphone, a smartwatch or a wristband for example. The electronics modules 104 can also be communicatively coupled to a remote cloud server 110 over, for example, a wide area network such as the Internet.

Each remote processing device 108 and optional remote cloud server 110 typically includes a processing unit, an output device (such as a display, speaker, or tactile feedback device), a user interface, an interface unit for communicating with other devices, Input/Output (I/O) hardware, a wireless unit (e.g. a radio that communicates using CDMA, GSM, GPRS or Bluetooth protocol according to standards such as IEEE 802.11a, 802.11b, 802.11g, or 802.11n), a power unit and a memory unit. The memory unit can include RAM, ROM, one or more hard drives, one or more flash drives or some other suitable data storage elements such as disk drives, etc.

The processing unit controls the operation of the remote processing device 108 or the remote cloud server 110 and can be any suitable processor, controller or digital signal processor that can provide sufficient processing power depending on the desired configuration, purposes and requirements of the system 100.

The display can be any suitable display that provides visual information. For instance, the display can be a cathode ray tube, a flat-screen monitor and the like if the remote processing device 108 or remote cloud server 110 is a desktop computer. In other cases, the display can be a display suitable for a laptop, tablet or handheld device such as an LCD-based display and the like.

System 100 can generally be used for determining user-specific weights and synthesizing sensors readings using the user-specific weights based on sensor readings received from a plurality of sensors. In some cases, system 100 may also track additional parameters or derived data from the synthesized sensor readings. The sensor readings, user-specific weights, synthesized sensor readings, and derived data may be monitored, stored, and analyzed for the user. Aspects of the monitoring, storage and analysis of biometric features and other metrics may be performed by one or more of the input unit 102, and/or a remote processing device 108, and/or the cloud server 110.

A remote cloud server 110 may provide additional processing resources not available on the input unit 102 or the remote processing device 108. For example, some aspects of processing the sensor readings acquired by the sensors 106 may be delegated to the cloud server 110 to conserve power resources on the input unit 102 or remote processing device 108. In some cases, the cloud server 100, input unit 102 and remote processing device 108 may communicate in real-time to provide timely feedback to a user regarding the sensor readings, synthesized sensor readings and data derived therefrom.

Referring now to FIG. 2A, shown therein is an example of an insole 200 that includes a sensing unit 202. The insole 200 is an example of an input device 102 that may be used in the system 100 shown in FIG. 1. The insole 200 may be used to provide a plurality of force sensors for a footwear insert, such as the insert described in PCT Application No. PCT/CA2020/051520, the entirety of which is incorporated herein by reference.

The insole 200 includes a sensor unit 202 and an optional liner 204. The liner 204 can provide a protective surface between the sensor unit 202 and an individual's foot. The liner 204 may have a slightly larger profile as compared to the sensor unit 202. That is, the outer perimeter 203 of the sensor unit 202 may be inwardly spaced from the outer perimeter 205 of the liner 204 by an offset 208. The offset 208 may be substantially consistent throughout the perimeter of the sensor unit 202 such that the sensor unit 202 is completed covered by the liner 204.

The sensor unit 202 can also include a connector 206. The connector 206 may provide a coupling interface between the plurality of sensors 106 and an electronics module (not shown) such as electronics module 104. The coupling interface can allow signals from the sensors 106 to be transmitted to the electronics module. In some cases, the coupling interface may also provide control or sampling signals from the electronics module to the sensors 106.

FIG. 2B illustrates the sensor unit 202 with the liner 204 omitted. Sensor unit 202 is an example of a sensor unit that may be used as sensing unit 105 in system 100. As illustrated, the plurality of sensors 106 are arranged in a predetermined pattern (also referred to as a sensor layout or predetermined sensor layout) where the sensors 106 are spaced apart from one another. The sensors 106 provide a set of discrete sensors that are distributed across the sensor unit 202.

In this layout, there are void locations where no actual sensor readings can be acquired. The void locations can include interstitial locations 220 between the sensors 106 where no actual sensor readings can be acquired. The void locations can also include external void locations 230 outside of the sensors 106 where no actual sensor readings can be acquired.

The predetermined pattern of sensors 106 can include at least 32 locations. As illustrated in the example of FIG. 2B, the predetermined pattern of sensors 106 in sensor unit 202 includes exactly 32 locations.

The arrangement of sensors 106 in the insole 202 can be separated into distinct regions or portions. As shown in FIG. 2B, in the example shown, the sensors 106 are separated into a forefoot portion 222, a midfoot portion 224, and a heel portion 226. The pattern of the sensors 106 within each portion (i.e. forefoot 222, midfoot 224 and heel 226) can be tailored based on the type and location of foot contact that is expected.

As illustrated, the sensor pattern includes sensors 106 arranged in a 2-3-4-4-4-3 arrangement in the forefoot portion 222. This forefoot sensor pattern may be particularly advantageous in acquiring sensor readings from the front part of an individual's foot, and the toe region in particular.

As illustrated, the sensor pattern includes sensors 106 arranged in a 1-1-1 arrangement in a midfoot portion 224. This midfoot sensor pattern may be particularly advantageous in acquiring sensor readings from the arch region of an individual's foot while also minimizing the total number of sensors required.

As illustrated, the sensor pattern includes sensors 106 arranged in a 2-1-2-1-2-1 arrangement in a heel portion 226. This sensor pattern may be particularly advantageous in acquiring sensor readings from the back part of an individual's foot, and the heel region in particular.

Figure 3:
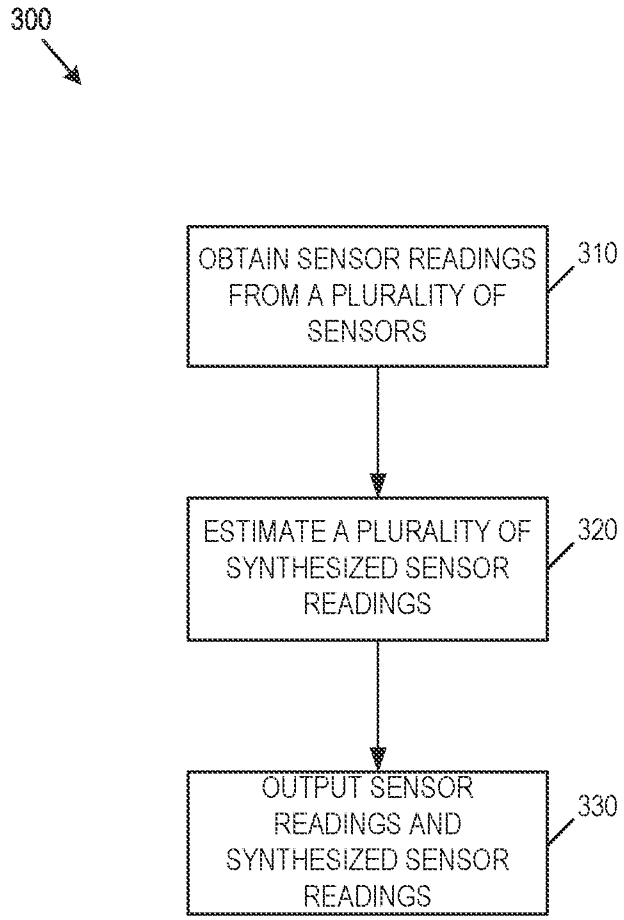
FIG. 3 is a flowchart illustrating an example of a method for synthesizing sensor data.

Referring now to FIG. 3, shown therein is an example method 300 for synthesizing sensor data for a carrier unit such as a wearable device or fitness equipment. The method 300 may be used with a plurality of sensors configured to measure human movement or human activity, such as sensors 106 for example. Method 300 is an example of a method for synthesizing sensor data in which user-specific estimation weights are defined so as to increase the accuracy of the synthesized sensor readings.

At 310, a plurality of sensor readings can be obtained from a corresponding plurality of sensors. The sensors can be positioned at specified locations on a carrier unit such as a wearable device or a piece of equipment.

The plurality of sensors can be arranged in a first predetermined pattern, such as the pattern shown in FIG. 2B. The first predetermined pattern can map each of the plurality of sensors to respective locations on the carrier unit. Accordingly, when the carrier unit is engaged with an individual's body, the sensors can be mapped to respective locations on the individual's body.

The first predetermined pattern can include different numbers of sensor locations depending on the type of carrier unit and/or the type of sensor. For example, the first predetermined pattern can include at least 32 locations. At least 32 sensor locations may be particularly desirable where the sensor unit is arranged to acquire data from under an individual's foot in order to allow the synthesized sensor readings to be estimated accurately.

The sensors can be configured to measure data relating to human activity. As shown in FIGS. 2A-2B, the plurality of sensors may be force sensors mapped to specific locations of an insole. The force sensors can measure force applied to the insole during physical activities, such as walking, running, jumping, or cycling for example.

At 320, the processor can determine a plurality of synthesized sensor readings for a corresponding plurality of synthesized sensors. The plurality of synthesized sensor readings can be estimated based on the plurality of sensor readings from 310 and a plurality of estimation weights. The estimation weights can be a plurality of user-specific weights calculated for the user (e.g. user-specific estimation weights determined using method 400 as described herein below).

The plurality of synthesized sensors can be arranged in a second predetermined pattern. The second predetermined pattern can map each of the plurality of synthesized sensors to respective locations on the carrier unit. Accordingly, when the carrier unit is engaged with an individual's body, the synthesized sensors can be mapped to respective locations on the individual's body.

The second predetermined pattern can include different numbers of sensor locations depending on the type of carrier unit, the type of sensor and/or the number and arrangement of sensor locations in the first predetermined pattern.

The second predetermined pattern can include the same number of locations as the first predetermined pattern. For example, the second predetermined pattern may include at least 32 locations.

The second predetermined pattern may include a greater number of locations than the first predetermined pattern. For example, the second predetermined pattern may include at least 68 locations.

The plurality of sensor readings received at 310 can be received from discrete sensors arranged at specified locations on a carrier unit according to the first predetermined pattern. The plurality of synthesized sensors can include synthesized sensors arranged at void locations where no discrete sensors are located according to the second predetermined pattern. The synthesized sensor readings can thus reflect an estimate of what an actual sensor would have measured had an actual sensor been positioned at the void location of a given synthesized sensor.

The void locations can include interstitial locations between the discrete sensors. The void locations can also include external void locations at locations external to the set of discrete sensors.

The set of sensor locations in the second predetermined pattern can be different from the set of sensor locations in the first predetermined pattern. In some examples, the set of sensor locations in the second predetermined pattern can be mutually exclusive of the set of sensor locations in the first predetermined pattern. Accordingly, each of the synthesized sensor readings may reflect estimated sensor readings at locations where there are no actual sensors.

Figure 4:
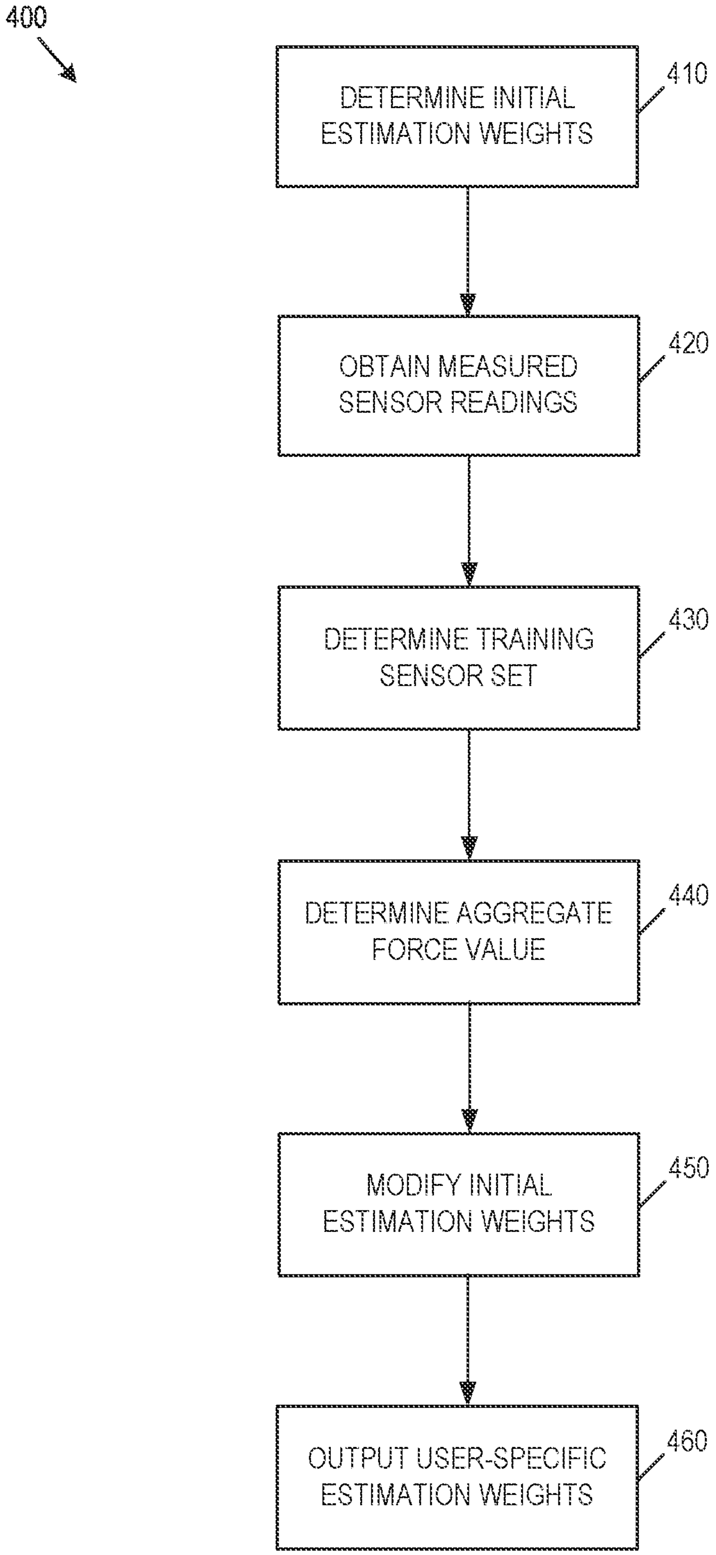
FIG. 4 is a flowchart illustrating an example of a method for determining user-specific estimation weights that may be used with the method shown in FIG. 3.

The plurality of estimation weights may be predetermined in a preprocessing phase. The preprocessing phase can be defined to optimize the estimation weights to minimize the error between the synthesized sensor readings and the readings that would have been acquired from an actual sensor positioned at the same location. The preprocessing phase can include an initial user training process in which sensor readings are obtained from a user while performing one or more predefined actions. An example method for determining the plurality of estimation weights during a preprocessing phase is shown in FIG. 4 and described in further detail herein below.

At 330, the processor can output the plurality of sensor readings and the plurality of synthesized sensor readings. This may provide a comprehensive set of sensor readings (real and estimated) across an area of an individual's body that is being measured or monitored. This set of sensor readings can be output directly through an output device to provide an individual with feedback on the activity being monitored. Alternately or in addition, the sensor readings may be stored, e.g. for later review, comparison, analysis, or monitoring.

Optionally, additional parameters or derived data values can be determined from the set of sensor readings (including the readings received at 310 and estimated at 320). These additional parameters may also be output to an individual as feedback, to a storage device, or to an analysis device or applications.

As noted above, the sensors may be force sensors mapped to specific locations of an insole. Accordingly, at 330, the controller may output a force grid that includes both the actual force measurements from the discrete sensors and the estimated force estimates from the synthesized sensors. The force grid can identify the force applied at all locations of the insole, including locations that do not have an actual sensor.

The controller can use the plurality of sensor readings and the plurality of synthesized sensor readings to compute force derivative values or force-based metrics. For example, the controller may use the plurality of sensor readings and the plurality of synthesized sensor readings to compute a vertical ground reaction force (vGRF).

Alternately or in addition, the controller can use the plurality of sensor readings and the plurality of synthesized sensor readings to compute a center of pressure (COP).

Alternately or in addition, the controller can use the plurality of sensor readings and the plurality of synthesized sensor readings to compute one or more additional parameters such as a foot contact event, a vertical rate of force development, impulse, a force map, a location of peak force, a COP velocity in two dimensions, a COP length in two dimensions, an anterior-posterior ground reaction force, and a medial-lateral ground reaction force for example.

Referring now to FIG. 4, shown therein is an example method 400 of determining user-specific estimation weights, which may be used to synthesize sensor readings, for example using method 300. The user-specific estimation weights may be used to improve the accuracy of estimated force sensor data at void locations on a sensor array. This can provide a user with more accurate movement and activity data.

Method 400 is an example of an initial training or preprocessing method that can be used to generate user-specific estimation weights for a particular user. The method 400 may be performed once by a user when determining the estimation weights for a particular sensor array (e.g. when the user first receives an insole incorporating a sensor array). The user-specific estimation weights generated through method 400 can be stored for subsequent use in synthesizing sensor readings for that user when they are using the corresponding sensor array.

Optionally, the user-specific estimation weights may also be used to synthesize sensor readings for that user when they are using a different sensor array with sensors arranged in the same first predetermined pattern. However, changing the sensor array or the wearable device containing the sensor array may affect the sensor readings, for instance if the sensor locations change relative to the user's body. Accordingly, a user may repeat method 400 when using a new sensor array and/or a new wearable device containing the same or different sensor array.

At 410, initial estimation weights can be determined. The initial estimation weights can be determined in various ways.

For example, the initial estimation weights can include interpolation weights. Sensor estimates (also referred to as synthesized sensor readings) at the interstitial locations defined by the second predetermined pattern can be calculated by interpolation based on sensor readings from one or more generic users at the locations of the discrete sensors used in the first predetermined pattern. Various methods of interpolation may be used, such as linear interpolation or cubic interpolation for example.

Through this initial interpolation, an initial set of interpolation weights can be defined. For example, linear interpolation produces interpolation weights for each interstitial location, which are multiplied by the measurements taken by neighboring discrete sensors to produce an estimate of the sensor measurement at the interstitial location.

The estimation weights can include extrapolation weights. For example, sensor estimates at the external void locations defined by the second predetermined pattern can be calculated by extrapolation based on sensor readings from one or more generic users at the locations of the discrete sensors used in the first predetermined pattern. Various methods of extrapolation may be used, such as linear extrapolation for example.

Through this initial extrapolation, an initial set of extrapolation weights can be defined. For example, linear extrapolation produces extrapolation weights for each external void location, which are multiplied by the measurements taken by neighboring discrete sensors to produce an estimate of the sensor measurement at the external void location.

Optionally, the initial estimation weights may include generically-optimized estimation weights that have been optimized based on training data collected from a plurality of users. For example, applicant's co-pending patent application Ser. No. 17/988,468 filed on Nov. 16, 2022 entitled "SYSTEM AND METHOD FOR SYNTHESIZING SENSOR READINGS", describes a preprocessing phase during which estimation weights are defined. The preprocessing phase described in co-pending patent application Ser. No. 17/988,468 involves filtering training data, generating initial estimation weights for void locations, then optimizing the estimation weights to minimize the error between synthesized data and a reference dataset. The estimation weights determined through the preprocessing phase described in co-pending patent application Ser. No. 17/988,468 may be used as the initial estimation weights at step 410 of the initial training or preprocessing method 400.

Alternatively or in addition, the initial estimation weights can include a hybrid or combination of interpolation/extrapolation weights and generically-optimized estimation weights. The interpolation/extrapolation weights can be used as the initial estimation weights for a first set of specified void locations while the generically-optimized estimation weights are used as the initial estimation weights for a second set of specified void locations. For example, for void locations within the sensor envelope (i.e. interstitial locations) interpolation weights can be used as the initial estimation weights while the generically-optimized estimation weights are used for the external void locations (i.e. the synthesized sensor locations between the sensor envelope and the outer boundary of the sensing unit).

Using generically optimized estimation weights as the initial estimation weights may reduce the computation required to optimize the estimation weights for a given individual. Determining the generically optimized estimation weights does involve significant computation. However, minimal computation is required to modify these weights to individual users, since the generically optimized estimation weights are expected to be close to the optimal solution. By contrast, if the initial interpolation and extrapolation weights are used as the initial estimation weights, significant computation would still be required to obtain the user-specific weights for each user.

As should be apparent to a person of skill in the art, the values of the user-specific estimation weights may vary due to the selection of the initial estimation weights. That is, the values of the user-specific estimation weights that result from an implementation of method 400 can be different if interpolation weights are used as the initial estimation weights as compared to using the generically-optimized weights as the initial estimation weights, since the optimization may reach different local minima.

Using generically optimized estimation weights as the initial estimation weights may also allow the user-specific estimation weights to be generated with less training data, since the generically optimized estimation weights are expected to be close to the optimal solution. This may also increase the likelihood of the optimization reaching a global minimum as opposed to simply a local minimum.

At 420, a plurality of measured sensor readings can be obtained from a corresponding plurality of sensors in a sensor array. The plurality of sensors can be arranged in a first predetermined pattern, such as the pattern shown in FIG. 2B. The first predetermined pattern can map each of the plurality of sensors to respective locations on the carrier unit. Accordingly, when the carrier unit is engaged with an individual's body, the sensors can be mapped to respective locations on the individual's body.

The measured sensor readings can be obtained while a user performs one or more predefined actions. The user may be wearing a wearable device containing the plurality of sensors while performing the predefined action(s). Alternatively, the plurality of sensors may be mounted to equipment used by the user while performing the predefined action(s).

The plurality of measured sensor readings can include one or more measured sensor sets. Each measured sensor set can include the sensor readings collected while the user performs a corresponding predefined action.

The plurality of measured sensor readings can include a plurality of measured sensor sets. Each measured sensor set can correspond to a different predefined action (i.e. each measured sensor set can include sensor readings obtained while the user performs a different predefined action).

The plurality of measured sensor sets can be obtained during a single data collection session (e.g. a training or set-up session) for the user. This can ensure consistency in the user's bodyweight (including the weight of the user's clothing and accessories), footwear, and the positioning of the sensors relative to the user's body.

Various different predefined actions may be performed by the user in order to collect the measured sensor sets. In some examples, each predefined action can correspond to a user standing in a static standing position. Accordingly, each measured sensor set can correspond to a particular static standing position.

The user may be prompted to perform the one or more predefined actions, for example through a computing device (e.g. through an app operating on their smartphone or computer). Where the predefined actions are static standing positions, the user can be prompted to stand in one or more static stances. Measured sensor sets can be determined based on sensor readings obtained while the user is standing in the static positions.

Optionally, the measured sensor sets can be determined based on an analysis of the sensor readings to detect that the user is in a static position. The sensor readings can be analyzed to detect sensor readings indicating that the user is currently in a static position. For example, determining that the sensor readings have stabilized (i.e. are unchanging) or that derived parameters such as the COP or ground reaction force have stabilized (i.e. are unchanging) can indicate that the user is in a standing position.

The static standing positions can include a plurality of different static standing positions. This can allow the measured sensor sets to include an assortment of force distributions. This may improve the accuracy of the user-specific estimation weights for synthesizing sensor readings while a user is performed different static and dynamic actions.

Each static standing position can be predefined to specify the portion or portions of a user's foot or feet that are in contact with the ground. The static standing positions can include one-footed standing positions (e.g. right foot flat, left foot flat, right foot toe balance, left foot toe balance, right foot heel balance, left foot heel balance etc.). Alternatively or in addition, the static standing positions can include two-footed standing positions (e.g. both feet flat, both feet toe balance, both feet heel balance etc.).

Alternatively or in addition, the predefined actions can include one or more dynamic stance actions. For example, a user may perform the predefined actions while using fitness equipment (e.g. a force-instrumented treadmill) that includes force plates usable to measure the forces applied in addition to the sensor array.

At 430, one or more training sensor sets can be determined for the user. The training sensor sets can be used to modify the initial estimation weights (from 410) in order to provide user-specific estimation weights.

The one or more training sensor sets can include a training sensor set for each measured sensor set. Each training sensor set can include the sensor readings from the corresponding measured sensor set as well as synthesized sensor readings at void location based on those sensor readings. Each training sensor set corresponds to the predefined action that also corresponds to the measured sensor set contained within that training sensor set.

A plurality of synthesized sensor readings can be estimated for a corresponding plurality of synthesized sensors based on the plurality of measured sensor readings (from 420) from that measured sensor set and the plurality of initial estimation weights (from 410). The plurality of synthesized sensors can be arranged in a second predetermined pattern. The second predetermined pattern can map each of the plurality of synthesized sensors to respective void locations of the sensor array. The training sensor set can then include the plurality of synthesized sensor readings and the sensor readings of the corresponding measured sensor set.

At 440, at least one aggregate force value can be determined based on the at least one training sensor set from 430. An aggregate force value can be determined for each training sensor set from 430.

As explained at 430, the at least one measured sensor set can include a plurality of measured sensor sets. Each measured sensor set can correspond to a different predefined action. A plurality of aggregate force values can be determined based on the training sensor sets corresponding to the plurality of measured sensor sets.

Each training sensor set (including the measured sensor readings and the synthesized sensor readings) can provide a force grid at all locations of the sensor array. The aggregate force value for that training sensor set can then be calculated from the force grid.

At 450, the user-specific weights can be determined by modifying the initial estimation weights based on the at least one aggregate force value. The initial estimation weights can be adjusted to minimize error values that are determined based on the at least one aggregate force value.

For example, at least one error value can be determined based on the at least one aggregate force value. The user-specific weights can then be determined by modifying the initial estimation weights to reduce the at least one error value.

Optionally, the at least one error value can be determined by comparing pairs of aggregate force values from the plurality of aggregate force values. For example, the relative error value can be determined based on a difference in the total force magnitude of the aggregate force values in a corresponding pair of aggregate force values.

That is, the relative error value can be determined as the difference between the aggregate force value (e.g. total force magnitude) corresponding to different predefined actions (e.g. $error_1=|F_{aggregatebothfeetflat}-F_{aggregatemeanrighttoe}|$, $error_2=|F_{aggregatebothfeetflat}-F_{aggregateleftheel}|$, etc.). Since the user's bodyweight should remain consistent for each predefined action, the aggregate force value should also remain the same.

Alternatively or in addition, the at least one error value can be determined by comparing aggregate force values to the mean of all aggregate force values obtained for the user during a particular data collection session. The aggregate force values should remain consistent for the data collection session, although there may be slight variations between different data collection sessions even for the same user (e.g. due to changes in bodyweight).

For example, the at least one error value can include at least one relative error value. Each relative error value can be determined based on a difference in the total force magnitude of an aggregate force value and the mean of all aggregate force values for the data collection session. This may simplify the process of determining the error value, since there it is not necessary to identify the particular predefined action being performed for any of the aggregate force values.

That is, each relative error value can be determined as the difference between the aggregate force value (e.g. total force magnitude) and the mean aggregate force value for all predefined actions (e.g. $error=|F_{aggregate}-F_{aggregatemean}|$). Since the user's bodyweight should remain consistent for each predefined action, the aggregate force value should also remain the same.

Alternatively or in addition, the at least one error value can include at least one absolute error value. The aggregate force value is expected to be equal to the user's bodyweight. Accordingly, each absolute error value can be determined based on a difference in the total force magnitude between a particular aggregate force value and a known bodyweight of the user (e.g. $error=|F_{bodyweight}-F_{aggregate}|$).

As noted above, the predefined actions can include static standing positions for a single foot and/or both feet of a user. Where the predefined action is a one-footed standing position, the aggregate force value from that one foot can be compared directly to the bodyweight. However, where the predefined action is a two-footed standing position, the aggregate force value should be determined as a sum from both feet prior to determining the difference between the aggregate force value and the user's bodyweight or determining the difference between the aggregate force value and the mean aggregate force value.

As noted herein above, the predefined actions may include one or more dynamic stance actions. In such cases, the error values may be determined by comparing the aggregate force value from the sensor array with the aggregate force value measured by the force plate. For example, a relative error value can be determined based on a difference in the total force magnitude of the aggregate force value from the sensor array and the aggregate force value from the force plate. This process may require additional processing to ensure that the force values measured by the force plate are aligned both spatially and temporally with the force values measured by the sensor array.

A cost function can be determined based on the at least one error value. Optionally, the at least one error value can include a plurality of error values. The cost function can be determined based on the plurality of error values. Various different types of cost functions may be used, such as root-mean square error and mean square error for example.

To determine the user-specific weights, the initial estimation weights can be modified in order to optimize the cost function. The initial estimation weights can be modified using an optimization algorithm in order to optimize the cost function. An iterative optimization method may be implemented to modify the estimation weights and evaluate the resultant error values until the cost function is minimized (e.g. until the error values are minimized). Various different types of optimization algorithms may be used, such as gradient descent optimization, least squares optimization and so forth.

Alternatively or in addition, the optimization algorithm can be provided as part of a machine learning model trained to output a reference force (body weight) from a measured force, by modifying the estimation weights. The model can be defined such that once a minimum is reached, the model can output a set of user-specific estimation weights. Various different types of machine learning models may be used, such as linear machine learning models and nonlinear machine learning (e.g. artificial neural networks).

Optionally, all of the initial estimation weights determined at 410 are modifiable at step 450. Alternatively, some of the initial estimation weights may be fixed while others are modifiable at 450. For example, a subset of the initial estimation weights may be fixed during the optimization process to reduce computation. The subset of initial estimation weights may be selected as estimation weights found to be consistently accurate across different user populations.

Optionally, sensor calibration factors can also be included as modifiable variables in the optimization process. Resistance values from each of the sensors in the sensor array can be measured while the sensor readings are obtained at 420. These resistance values can be mapped to the corresponding force value output by the sensor. A model or function can be used to map the resistance values to the corresponding force value output. The parameters of the function/model can be determined for each sensor following the process of collecting sensor readings and identifying the transformations from the resistance values to the resulting force value output. The error values from 440 used to determine the user-specific weights can also be used to optimize the calibration parameters for the individual sensors.

At 460, the user-specific weights can be output. The user-specific weights can be output for storage in a non-transitory storage medium of a device such as the input unit 102, processing device 108 and/or cloud server 110. The user-specific weights can subsequently be accessed and used to analyze sensor readings obtained for the user (e.g. as part of a method for synthesizing sensor readings such as method 300).

Optionally, outputting the user-specific weights can include storing the user-specific weights locally in a non-transitory storage module of a wearable device or fitness equipment containing the plurality of sensors. This can allow the synthesized force readings, and associated force data to be calculated for a user in real-time. For example, the user-specific estimation weights can be loaded onto the firmware of an insole such as insole 200 during a firmware update.

Alternatively or in addition, the user-specific weights can be stored remotely from the wearable device or fitness equipment containing the plurality of sensors. The user-specific weights can then be accessed when analyzing sensors readings obtained for the user.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method of determining user-specific weights usable to synthesize sensor data at void locations of a sensor array, the method comprising:

determining a plurality of initial estimation weights for the void locations of the sensor array, wherein the void locations of the sensor array correspond to locations of the sensor array between discrete sensors or outside a set of the discrete sensors;

obtaining a plurality of measured sensor readings from a corresponding plurality of sensors in the sensor array, wherein the plurality of sensors is arranged in a first predetermined pattern, wherein the first predetermined pattern maps each of the plurality of sensors to respective locations on a carrier device, wherein the plurality of measured sensor readings includes a plurality of measured sensor sets, wherein each measured sensor set is collected while a user performs a corresponding predefined action, the plurality of measured sensor sets being obtained during a single data collection session for the user such that a bodyweight of the user remains consistent across the plurality of measured sensor sets;

determining a training sensor set for each measured sensor set by:

estimating a plurality of synthesized sensor readings for a corresponding plurality of synthesized sensors based on the plurality of measured sensor readings from that measured sensor set and the plurality of initial estimation weights, wherein the plurality of synthesized sensors is arranged in a second predetermined pattern, and wherein the second predetermined pattern maps each of the plurality of synthesized sensors to respective void locations of the sensor array; and determining the training sensor set to include the measured sensor readings from that measured sensor set and the corresponding plurality of synthesized sensor readings;

determining the user-specific weights by:

determining a plurality of aggregate force values each based on a corresponding training sensor set;

modifying the plurality of initial estimation weights based on the plurality of aggregate force values; and outputting the user-specific weights;

wherein determining the plurality of aggregate force values comprises, for each corresponding training sensor set, generating, from that training sensor set, a force grid that represents forces at locations of the sensor array including the void locations by combining the measured sensor readings and the synthesized sensor readings, and calculating each aggregate force value as a total force magnitude of the force grid, and wherein modifying the plurality of initial estimation weights comprises adjusting the plurality of initial estimation weights to reduce a difference between the total force magnitude of a given aggregate force value and a mean total force magnitude determined as a mean of the total force magnitudes of the plurality of aggregate force values obtained during the single data collection session.

2. The method of claim 1, wherein determining the user-specific weights comprises:

determining an additional error value based on the plurality of aggregate force values; and modifying the plurality of initial estimation weights to reduce the additional error value.

3. The method of claim 2, wherein each measured sensor set of the plurality of measured sensor sets corresponds to a different predefined action, and determining the user-specific weights comprises:

determining the additional error value by comparing pairs of aggregate force values from the plurality of aggregate force values.

4. The method of claim 3, wherein the additional error value includes at least one relative error value, each relative error value determined based on a difference in the total force magnitude of between the aggregate force values in a corresponding pair of aggregate force values.

5. The method of claim 3, wherein the at least one error value includes at least one relative error value, each relative error value determined based on a difference in the total force magnitude between a given aggregate force value and a mean aggregate force value of the plurality of aggregate force values.

6. The method of claim 3, wherein the at least one error value includes at least one absolute error value, each absolute error value determined based on a difference in the total force magnitude between a particular aggregate force value and a known bodyweight of the user.

7. The method of claim 2 further comprising:

determining a cost function based on the additional error value; and adjusting the initial estimation weights using an optimization algorithm to optimize the cost function.

8. The method of claim 1, wherein each predefined action corresponds to the user standing in a static standing position, and each measured sensor set corresponds to a particular static standing position.

9. The method of claim 1, wherein the carrier device is a wearable device configured to be worn on a foot of the user.

10. A system for determining user-specific weights usable to synthesize sensor data at void locations of a sensor array, the system comprising:

the sensor array comprising a plurality of sensors arranged in a first predetermined pattern, with each sensor of the plurality of sensors arranged at a respective location on a carrier device; and one or more processors communicatively coupled to the plurality of sensors, wherein the one or more processors is configured to:

obtain a corresponding plurality of measured sensor readings from the plurality of sensors in the sensor array, wherein the plurality of measured sensor readings includes a plurality of measured sensor sets, and each measured sensor set is collected while a user performs a corresponding predefined action, the plurality of measured sensor sets being obtained during a single data collection session for the user such that a bodyweight of the user remains consistent across the plurality of measured sensor sets;

determine a plurality of initial estimation weights for the void locations of the sensor array, wherein the void locations of the sensor array correspond to locations of the sensor array between discrete sensors or outside a set of the discrete sensors;

determine a training sensor set for each measured sensor set by:

estimating a plurality of synthesized sensor readings for a corresponding plurality of synthesized sensors based on the plurality of measured sensor readings from that measured sensor set and the plurality of initial estimation weights, the plurality of synthesized sensors arranged in a second predetermined pattern, wherein the second predetermined pattern maps each of the plurality of synthesized sensors to the respective void locations of the sensor array; and determining the training sensor set to include the measured sensor readings from that measured sensor set and the corresponding plurality of synthesized sensor readings;

determine the user-specific weights by:

determining a plurality of aggregate force values each based on a corresponding training sensor set;

modifying the plurality of initial estimation weights based on the plurality of aggregate force values; and output the user-specific weights;

wherein determining the plurality of aggregate force values comprises, for each corresponding training sensor set, generating, from that training sensor set, a force grid that represents forces at locations of the sensor array including the void locations by combining the measured sensor readings and the synthesized sensor readings, and calculating each aggregate force value as a total force magnitude of the force grid, and wherein modifying the plurality of initial estimation weights comprises adjusting the plurality of initial estimation weights to reduce a difference between the total force magnitude of a given aggregate force value and a mean total force magnitude determined as a mean of the total force magnitudes of the plurality of aggregate force values obtained during the single data collection session.

11. The system of claim 10, wherein the one or more processors is configured to determine the user-specific weights by:

determining an additional error value based on the plurality of aggregate force values; and modifying the plurality of initial estimation weights to reduce the additional error value.

12. The system of claim 11, wherein each measured sensor set of the plurality of measured sensor sets corresponds to a different predefined action, and the one or more processors is configured to determine the user-specific weights by:

determining the additional error value by comparing pairs of aggregate force values from the plurality of aggregate force values.

13. The system of claim 12, wherein the one or more processors is configured to determine the additional error value to include at least one relative error value, each relative error value determined based on a difference between the total force magnitude of the plurality of aggregate force values in a corresponding pair of aggregate force values or based on a difference in the total force magnitude between a given aggregate force value and a mean total aggregate force value of the plurality of aggregate force values, or to include at least one absolute error value, each absolute error value determined based on a difference in the total force magnitude between a particular aggregate force value and a known bodyweight of the user.

14. The system of claim 11, wherein the one or more processors is configured to:

determine a cost function based on the additional error value; and adjust the plurality of initial estimation weights using an optimization algorithm to optimize the cost function.

15. The system of claim 10, wherein each predefined action corresponds to the user standing in a static standing position, and each measured sensor set corresponds to a particular static standing position.

16. The system of claim 10, wherein the carrier device is a wearable device configured to be worn on a foot of the user.

17. The system of claim 10, wherein the sensors are force sensors, and the force sensors are positioned underfoot.

18. The system of claim 10, wherein the carrier device is a wearable device and the one or more processors is configured to output the user-specific weights by storing the user-specific weights in a non-transitory storage module of the wearable device.

* * * * *